(12) United States Patent
Woods

(10) Patent No.: US 6,649,567 B2
(45) Date of Patent: Nov. 18, 2003

(54) CONTROLLED RELEASE MICROBIOCIDE FOR POROUS SURFACES

(75) Inventor: William B. Woods, Hampton, NJ (US)

(73) Assignee: ISP Investments Inc., Wayne, NJ (US)

( * ) Notice: Subject to any disclaimer, the term of this patent is extended or adjusted under 35 U.S.C. 154(b) by 0 days.

(21) Appl. No.: 09/975,875

(22) Filed: Oct. 11, 2001

(65) Prior Publication Data

US 2003/0092575 A1 May 15, 2003

(51) Int. Cl.$^7$ .............................. A01N 35/02; B27K 3/36
(52) U.S. Cl. ...................... 504/150; 504/161; 504/348; 514/705; 428/540; 428/541
(58) Field of Search .................. 504/161, 150; 514/705; 428/540, 541

(56) References Cited

U.S. PATENT DOCUMENTS 5,917,094 A * 6/1999 Werle et al. ................ 568/449
6,383,569 B2 * 5/2002 Ornstein et al. ......... 427/389.7

FOREIGN PATENT DOCUMENTS

EP 0 667 358 * 1/1995

* cited by examiner

*Primary Examiner*—S. Mark Clardy
(74) *Attorney, Agent, or Firm*—Abelman, Frayne & Schwab

(57) ABSTRACT

Algal defacement of coated and non-coated porous masonry and wood construction materials is prevented by pre-treatment of the construction material with an aqueous composition of a copolymer that releases 2-propenal (acrolein) over time.

17 Claims, No Drawings

CONTROLLED RELEASE MICROBIOCIDE FOR POROUS SURFACES

FIELD OF THE INVENTION

The invention relates to the treatment of porous masonry and wood surfaces to control algal defacement by the application of a microbicidal composition.

BACKGROUND

Microbial colonization of masonry construction materials significantly contributes to defacement and weathering. This can be caused by a diverse community of microorganisms that includes bacteria, fungi and algae. Growth of these organisms and thus the severity of defacement and biodeterioration is dependent on many factors, including porosity of the masonry material, pore size and distribution, permeability, effective pH, surface charge, nutrient availability, presence of light, temperature and relative humidity and wetting by rain.

Physiochemical characteristics such as the porosity, pore size distribution, permeability, surface charge and alkalinity vary from material to material and even within samples of the same material. These characteristics can affect the performance of biocidal treatments. Consequently, performance and effective application-rate ranges must be based on the response of treated porous masonry and wood substrate materials to microbial challenge.

Typical approaches to the control of microbial growth on or from within masonry materials are (1) limitation of the moisture content of the construction material using water repellants, and (2) treatment with microbicidal chemicals. Chemical treatments that have been used with some success are: hypochlorite, organotin, organomercurial, quaternary ammonium salt, chlorinated phenolic, borate and phosphoric acid. The use of many of these chemical biocides has been restricted or entirely banned due to concerns for significant environmental impact. Some of the chemical treatments may not be supported under the European Union Biocidal Products Directive due to high costs.

Extreme cases of defacement have been observed of newly-constructed masonry surfaces (non-painted) and freshly painted masonry by algae commonly encountered in the warm humid climates of the Pacific Rim and Mediterranean regions of the world. Similar defacement has also been reported in temperate regions. If left untreated for an extended period of time, the masonry substrate can incur permanent damage, leading to attendant costs for repair and replacement.

It is known from U.S. Pat. No. 5,917,094 that a 2-propenal-releasing emulsion homopolymer can be produced by adding 2-propenal that is at least 95% by weight pure, to a composition of an alkali hydroxide under specified conditions, and then adjusting the pH to the range of from 5 to 7. The only use disclosed for such 2-propenal homopolymers are in aqueous systems, such as paints and other architectural coatings. The 2-propenal is released when a pH is greater than 7, thereby producing a biocidal affect in these systems. A controlled release of 2-propenal to maintain apparently minimum effective limit value of 0.7 ppm in the aqueous systems tested reportedly exceeded 400 days.

It is known from the prior art to use a 2-propenal copolymer as an in-can preservative to prevent spoilage of aqueous liquid products, such as decorative coatings, adhesives, metal working fluids and inks. When used in these industrial applications the 2-propenal copolymer is supplied in the form of an aqueous composition at about 50 weight percent as the copolymer and is mixed with the aqueous liquid composition, typically in a percentage by weight in the range of from about 0.25% to 1%.

It is also known from the prior art to add 2-propenal molecular or oligomer form to outdoor containments lined with polymer membranes, waste water storage, and treatment ponds and drainage ditches to control the growth of water-borne algae. Such applications do not appear to have included use of a 2-propenal copolymer.

The art has not been found to disclose the use of a copolymer of 2-propenal for application to solid porous surfaces to prevent the defacement of the surface by organisms that colonize such surfaces, e.g., terrestrial algae.

It is therefore a principal object of the invention to provide a safe and efficacious method for applying an environmentally benign composition having anti-microbial activity as an algacidal treatment for masonry and wood surfaces subject to algal growth and defacement.

It is also an object of this invention to provide a quantitative application rate for 2-propenal copolymers that will provide extended time-release anti-microbial protection for the surface of porous construction materials exposed to algal growth and defacement.

SUMMARY OF THE INVENTION

The above objects and other benefits and advantages are attained by the practice of the method of the invention in which a time-release aqueous biocidal composition of a 2-propenal copolymer is applied to the porous surface of a construction material selected from the group consisting of stone, concrete, brick and wood and the biocidal composition is maintained in contact with the porous surface for a sufficient period of time to saturate a portion of the construction material below the surface with the biocidal composition. The surface of the construction material is then allowed to dry.

If desired, after drying the surface of construction material can be coated with a decorative architectural coating, or paint.

As used herein, the term "2-propenal copolymer" means a composition of 2-propenal prepared in accordance with the disclosure of U.S. Pat. No. 6,060,571, the disclosure of which is incorporated herein by reference. A particularly preferred composition is the reaction product of 2-propenal and propylene 1,2-glycol prepared in accordance with Example 4 of U.S. Pat. No. 6,060,571 as described below.

In a preferred embodiment, the biocidal compound constitutes at least about 0.25% by weight of the aqueous composition applied to the construction material. In an especially preferred embodiment the 2-propenal copolymer is about one percent by weight of the applied composition.

The aqueous biocidal composition can be applied by conventional methods including spraying, brushing and dispensing a liquid stream from a horizontal feed line and allowing the composition to stream down the face of an existing structure.

In a particularly preferred embodiment, new construction materials are treated by immersing the construction material in a bath of the biocidal composition, or by dipping or soaking one of more of the surfaces of the material that will be exposed to biological growth in a treatment zone containing the biocidal composition. This method of application is particularly effective and efficient, since the duration of the soaking time in the specific concentration of the biocidal composition can be used to provide the desired degree of time-release protection. The depth of penetration and saturation can be determined from a relatively small sample of the particular construction material, whether it be a natural stone such as sandstone, a fired brick, a section of pre-cast concrete or so-called cast stone or any of the various species of wood that are used for construction. The immersion, dipping and soaking methods of application also have the particular advantage of assuring a uniform concentration of material over the entire surface treated, thereby avoiding potential problems is associated with the application of the aqueous biocidal composition by brushing or spraying to existing structures.

In a further preferred method of practicing the invention for providing a time-release protection to new construction materials, the individual elements, i.e., bricks, natural stone, concrete blocks or pre-cast articles, wood, or the like, are conditioned to a uniform moisture content prior to application of the biocidal copolymer composition. For example, when construction materials are stored in a climate having high humidity, it is preferred to dry at least the surface to be treated with the biocidal copolymer composition to dry out excessive moisture so that the region at the exposed surface can absorb the optimum volume of the applied composition.

It is well known in the wood products industry to kiln dry lumber to minimize twisting and other deformation that can occur to render the material unsuitable. Such dried or otherwise cured wood construction materials will be likely to absorb a predictable amount of the treating composition. Wooden construction materials -so treated can be further treated with other conventional preservatives in accordance with methods known to the art.

Several application methods are suitable for the practice of the invention in the treatment of seasoned wood products with aqueous preservative compositions, including thermal treatment and pressure treatment.

Thermal treatment also known as hot and cold bath treatment, involves immersion of the wood products in a hot preservative composition and then a cool preservative composition. The hot composition causes air in the wood to expand; the subsequent immersion in a cool preservative composition causes the air in the wood to contract creating a vacuum that draws preservative into the wood.

The invention can also be employed in prior art pressure treatments such as the full-cell and empty-cell processes. In the full-cell process, dry wood products are loaded into a retort and a vacuum is drawn to remove air from the wood. The preservative composition is then introduced into the retort. When the retort is filled with composition, pressure is applied to force the composition into the wood. When absorption is complete the pressure is released and the treated wood products are removed.

In the empty-cell process, preservative composition is introduced into the retort at atmospheric pressure and then the retort is pressurized. When absorption is complete, the pressure is released and the remaining preservative composition is withdrawn to storage. The pressure inside the retort is reduced to remove any excess preservative composition from the wood products. An advantage of this process over the full-cell process is that similar penetrations of the wood can be obtained with a reduced use of preservative composition. As will be understood by one of ordinary skill in the art from the above descriptions, the method and preservation system of the invention can be employed in other known treatment processes.

Exterior wooden surfaces that are coated with pigmented decorative paints also benefit from treatment of the wood substrate in accordance with the invention. These painted surfaces, as well as bare wooden surfaces, are subject to defacement by microorganisms such as highly colored filamentous algae. Treated wood serves as a source of the biocidal 2-propenal copolymer for longterm protection of painted surfaces from biological defacement. The 2-propenal copolymer composition can also be formulated with other biocidal compounds in order to broaden the spectrum of antimicrobial activity. Wetting agents, such as nonionic surfactants and cosolvents such as propyleneglycol can be used as adjuvants to promote adsorption of the preservative composition into woods that are otherwise difficult to penetrate.

Following treatment with the aqueous biocidal copolymer composition and drying of the surface, the construction material can be painted with a decorative architectural coating. Coating materials that have been found suitable for use in connection with the practice of the invention are acrylic, vinylacrylic and alkyd modified latex paints. These types of coatings are sufficiently porous to allow the active material to pass through and exhibit its biocidal activity. The painted surface also slows the leaching of the active compound at the surface when exposed to direct rainfall, water spray and the like.

As used herein, the terms "time-release" or "controlled release" means the essentially continuous release of an amount of biocidally active material that is effective to inhibit or control the growth of defacing and/or damaging algae for an extended period of time that exceeds about six months.

The advantages of treatment with a controlled or time-release copolymer include the following:

1. Treatment with the copolymer offers long-term protection versus that provided by short-term treatments, such as hypochlorite.
2. The copolymer is not a charged moiety and the binding to mineral surfaces that occurs with some cationic biocides does not occur.
3. The copolymer is not an inorganic nutrient, as is the residual phosphate from commonly-used masonry treatments containing phosphoric acid.
4. The copolymer is non-chlorinated and non-metallic and avoids the environmental concerns raised by the use of compositions containing chlorine and metals.

DETAILED DESCRIPTION OF THE INVENTION

The following examples and detailed description are provided to illustrate to one of ordinary skill in the art the method and products of the invention.

The first tier screening test described herein demonstrates the efficacy of the biocidal copolymer as an algaecidal treatment for masonry materials commonly used in Europe, the Pacific-Rim and the United States. Brick, sandstone and concrete were treated and challenged with an algal inoculum. The test results also establish appropriate application guidelines for the concentration and application rates of the 2-propenal copolymer compositions that are applied in situ to various uncoated construction materials.

Materials and Methods

In order to demonstrate the efficacy of the method of the invention, samples of materials representative of masonry products from different regions of the world were subjected to the test protocol. Masonry samples were treated and either (1) uncoated; or (2) coated with paint and then exposed to severe challenge with an inoculum of algae known to exhibit high growth activity in warm, humid climates. The tests were performed in microenvironments constructed of large petri dishes containing a nutrient medium. Surface defacement and zones of inhibition were rated according to established practice and photographed. A variety of pretreatment regimes were used to establish guidelines for application of a composition of 2-propenal copolymer.

Test Chamber

Test chambers simulating microenvironments were provided for the purpose of demonstrating the efficacy of the invention. Plastic petri dishes measuring 90 mm×250 mm. were partially filled with approximately 50 ml of Allen's nutrient agar medium. Masonry test specimens in the form of small blocks were placed on the hardened agar medium in the petri dishes and then inoculated with an algal cell suspension. The petri dishes were then placed in an incubator and the surface of the masonry blocks observed and rated for algal growth at weekly intervals for six weeks.

Inoculum

Five to fourteen day cultures of the green alga, Chlorella sp (ATCC 7516), were harvested to sterile distilled water and suspended. Each masonry block was inoculated with 1 ml of Chlorella sp suspension.

Preparation of Biocidal Compositions

Biocidal compositions ranging in concentration from 0.25 to 5.0 weight-percent of 2-propenal copolymer were prepared from an aqueous stock preparation of commercially available 50 weight-percent 2-propenal copolymer by dilution with water. The commercial product utilized in the work reported is sold under the trademark NUOSEPT® APC-P by Degussa Corporation of Parsippany, N.J.

Alternatively a composition that is the reaction product of 2-propenal and propylene 1,2-glycol is prepared in accordance with Example 4 of U.S. Pat. No. 6,060,571 as follows:

EXAMPLE A

A mixture of 725 ml. of propylene 1,2-glycol and 10 ml of 1N NaOH is prepared in a flask and 610 ml of 2-propenal are added at 10° C. with cooling. The mixture is kept in the temperature range of up to 35° C. and stirring is continued for about 1 hour at 40° C. The viscous yellow solution is neutralised by the addition of hydrochloric acid. The residual content or unreacted 2-propenal is about 0.01%.

Incubation

Petri dishes were incubated at 25° to 26° C. at an average relative humidity of 87% for six weeks under a light-dark cycle of 14:10 hours at a light illumination of 2000 to 3000 LUX.

Algal Growth Rating

The masonry blocks were rated weekly for growth using the following commonly used numerical system:

| Zone of Inhibition | Rating |
| --- | --- |
| No growth | 0 |
| Trace growth (<10%) | 1 |
| Light growth (10–30%) | 2–3 |
| Moderate growth (30–60%) | 4–6 |
| Heavy growth (60% to complete coverage) | 7–10 |

Masonry Test Block Preparation

Each test specimen was about 2.5 cm.×2.5 cm square (6.25 cm$^2$) and about 1 cm thick and weighed about 6 to 10 gm.

| Masonry Block Description | | |
| --- | --- | --- |
| Source | Masonry Type | pH |
| Singapore | Red Brick | 7.9 |
| Holland | Yellow Brick | 8.1 |
| Holland | Red Brick | 7.7 |
| Germany | Sandstone | 8.0 |
| USA | Concrete | 8.6 |

The pH was determined after one-week contact with water using a pH meter.

The blocks were treated by dipping the blocks in aqueous compositions of the biocidal copolymer prepared as described above at the following concentrations: 0.0% (untreated control); 0.25%, 0.5%, 2.5% and 5.0%.

After removing a block and allowing the block to drip dry for 30 to 60 minutes it was either placed in a petri dish (uncoated block) or coated with a masonry paint and allowed to dry 24 hours. The block was then placed in a petri dish. The blocks were surface-inoculated with 1 ml of algal cell suspension about 24 hours after placement in the petri dishes.

Results

The data which follows establish the efficacy of the method of the invention and the beneficial results from its practice on various construction materials.

Growth-Response

The test protocol included the following two conditions in the determination of biocidal activity: (1) the non-treated control sample of the construction material was susceptible to the microbial challenge; and (2) growth of the challenge microbe(s) must be controlled by the test microbicide, preferably with a response that indicates that activity is a function of the quantity or concentration of the microbicide present in the test block. The latter condition is referred to as dose-response.

Masonry Blocks (Non-coated)

The growth responses of the treated masonry blocks (non-coated) presented in Tables 1 through 5 clearly show that treatment with the biocidal copolymer at a concentration of 0.5% or greater prevents the growth of the algal challenge. The Singapore Red Brick, Holland Yellow Brick, Holland Red Brick, German Sandstone and USA Concrete all responded consistently to treatment with the copolymer.

The test results on the Singapore Red Brick are particularly noteworthy because of the magnitude of the difference in the grow ratings of the unprotected control and the treated blocks. With reference to Table 1, the control exhibits significant growth within 2 weeks with a rating of 4 (40% surface coverage) increasing to 9 (90% coverage) by the fourth week. The treated blocks illustrate a dose-response growth-rating history. Protection at 0.25% is improved versus the control with the treated block showing a rating of 1 (trace surface growth) at two weeks and a growth rating of 2 at the fourth week. A dramatic improvement in performance occurs when the brick sample block is treated with compositions having a concentration of 0.5% and 2.5% of the copolymer. The growth rating never exceeds a value of 0 (zone of inhibition with no surface growth) when treated with a composition of the copolymer at a 2.5% or greater concentration.

Each of the other masonry materials, i.e., German Sandstone, Holland Yellow Brick, Holland Red Brick and USA Concrete, show similar results. (See Tables 2 through 5 below). In each case, a breakpoint occurs at 0.5% copolymer treatment. When the 0.5% treatment is tested in an exterior exposure series, similar results are discovered. This treatment corresponds to an application rate of approximately 0.5 to one liter of a 0.5% aqueous composition of copolymer per square meter of surface.

Masonry Blocks (Painted)

As described above, a set of masonry blocks was treated and then coated with a masonry paint. These blocks were then challenged with the algal inoculum as previously described and observed for growth.

The growth responses closely parallel those of the non-coated blocks, with the exception that the coated blocks were uniformly less susceptible to defacement. The results of the Painted Singapore Red Brick (Table 6) clearly illustrates the difference. The breakpoint in protection occurs at 0.5% copolymer treatment; however, the algal growth response for the coated control at 6-weeks is 2 compared to a rating of 9 for the non-painted control block.

These results are of particular interest because they surprisingly indicate that the porous block can act as a biocidal reservoir for the copolymer and the copolymer is then transported through the porous coating to provide long-term protection of the paint from surface defacement.

Susceptibility of Unprotected Masonry Blocks

At the completion of the study it was noted that the concrete masonry material (USA Concrete) was not as susceptible to defacement as the other masonry materials. (See Table 7, Susceptibility of Masonry to Algal Defacement.) A lack of facile attachment sites for the algal cell mass to the concrete sample block surface (a cross-sectional cut) can be responsible for this observed result. Comparison of the cross-sections of the different block materials shows that the concrete is heterogeneous and that it contains numerous large-sized aggregate stones as compared to the homogenous brick (mostly clay) and sandstone. The concrete cross-section sample shows a high percentage of hard, non-porous stones having a cumulative sectional area of about 50% of the total block cross-section.

Another factor affecting observed growth can be pH. A moist acidic or extremely alkaline surface would be expected to inhibit colonization by algae; however, in this case the pH of the concrete was moderate at 8.6 which value was not greatly different than the other materials. Consequently, it was concluded that in this case the pH of the moist concrete surface did not significantly affect the growth of the algal inoculum.

Treatment of Wood

Treatment of dry wood with an aqueous composition containing 0.5 percent by weight of the copolymer using a thermal or pressure process typically produces a retention of about 2 kg of 2-propenal copolymer per one cubic meter volume of wood. A retention of this magnitude is obtained in the laboratory using seasoned white pine (*Pinus strobus*) and a simplified thermal process as described below.

A small block of the test specimen is heated in a manual autoclave under about 1 atmosphere of pressure to a temperature of about 120° C. The pressure is then released, the specimen removed and treated by immersion in a cool aqueous solution of the biocidal copolymer. Temperature can be controlled using a water bath at 20° C. After several hours the specimen is removed and air-dried. Control specimens are prepared in a similar fashion with the exception that the samples are immersed in water that does not contain any biocidal compounds.

Microbial challenge with an algal inoculum is performed as previously described. Coated and non-coated test specimens are evaluated and typical results are presented in Table 8.

TABLE 1

Singapore Red Brick
Growth Rating

| Concentration (Weight %) | Time (Weeks) | | | | | |
|---|---|---|---|---|---|---|
| | 1 | 2 | 3 | 4 | 5 | 6 |
| 0.00 | 2 | 4 | 7 | 9 | 9 | 10 |
| 0.25 | 1 | 1 | 1 | 2 | 2 | 2 |
| 0.50 | 0 | 0 | 1 | 1 | 1 | 1 |
| 2.50 | 0 | 0 | 0 | 0 | 0 | 0 |
| 5.00 | 0 | 0 | 0 | 0 | 0 | 0 |

TABLE 2

Germany Sandstone
Growth Rating

| Concentration (Weight %) | Time (Weeks) | | | | | |
|---|---|---|---|---|---|---|
| | 1 | 2 | 3 | 4 | 5 | 6 |
| 0.00 | 2 | 2 | 2 | 2 | 2 | 2 |
| 0.25 | 1 | 1 | 1 | 1 | 1 | 1 |
| 0.50 | 0 | 0 | 0 | 0 | 0 | 0 |
| 2.50 | 0 | 0 | 0 | 0 | 0 | 0 |
| 5.00 | 0 | 0 | 0 | 0 | 0 | 0 |

TABLE 3

Holland Yellow Brick
Growth Rating

| Concentration (Weight %) | Time (Weeks) | | | | | |
|---|---|---|---|---|---|---|
| | 1 | 2 | 3 | 4 | 5 | 6 |
| 0.00 | 1 | 10 | 10 | 10 | 10 | 10 |
| 0.25 | 0 | 0 | 0 | 0 | 0 | 0 |
| 0.50 | 0 | 0 | 0 | 0 | 0 | 0 |
| 2.50 | 0 | 0 | 0 | 0 | 0 | 0 |
| 5.00 | 0 | 0 | 0 | 0 | 0 | 0 |

TABLE 4

Holland Red Brick
Growth Rating

| Concentration (Weight %) | Time (Weeks) | | | | | |
|---|---|---|---|---|---|---|
| | 1 | 2 | 3 | 4 | 5 | 6 |
| 0.00 | 1 | 2 | 2 | 2 | 2 | 2 |
| 0.25 | 0 | 1 | 1 | 1 | 1 | 1 |
| 0.50 | 0 | 0 | 0 | 0 | 0 | 0 |
| 2.50 | 0 | 0 | 0 | 0 | 0 | 0 |
| 5.00 | 0 | 0 | 0 | 0 | 0 | 0 |

TABLE 5

USA Concrete
Growth Rating

| Concentration (Weight %) | Time (Weeks) | | | | | |
|---|---|---|---|---|---|---|
| | 1 | 2 | 3 | 4 | 5 | 6 |
| 0.00 | 1 | 1 | 1 | 1 | 1 | 1 |
| 0.25 | 0 | 1 | 1 | 1 | 1 | 1 |
| 0.50 | 0 | 0 | 0 | 0 | 0 | 0 |
| 2.50 | 0 | 0 | 0 | 0 | 0 | 0 |
| 5.00 | 0 | 0 | 0 | 0 | 0 | 0 |

TABLE 6

Painted Singapore Red Brick
Growth Rating

| Concentration (Weight %) | Time (Weeks) | | | | | |
|---|---|---|---|---|---|---|
| | 1 | 2 | 3 | 4 | 5 | 6 |
| 0.00 | 1 | 1 | 2 | 2 | 2 | 2 |
| 0.25 | 1 | 1 | 1 | 1 | 1 | 1 |
| 0.50 | 0 | 0 | 0 | 0 | 0 | 0 |
| 2.50 | 0 | 0 | 0 | 0 | 0 | 0 |
| 5.00 | 0 | 0 | 0 | 0 | 0 | 0 |

TABLE 7

Susceptibility of Masonry to Algal Defacement
Growth Rating

| Masonry Type | Time (Weeks) | | | | | |
|---|---|---|---|---|---|---|
| | 1 | 2 | 3 | 4 | 5 | 6 |
| Singapore Red Brick | 2 | 4 | 7 | 9 | 9 | 10 |
| Germany Sandstone | 2 | 2 | 2 | 2 | 2 | 2 |
| Holland Yellow Brick | 1 | 10 | 10 | 10 | 10 | 10 |
| Holland Red Brick | 1 | 2 | 2 | 2 | 2 | 2 |
| USA Concrete | 1 | 1 | 1 | 1 | 1 | 1 |

TABLE 8

White Pine Projected Results
Growth Rating

| Concentration (Weight %) | Time (Weeks) | | | | | |
|---|---|---|---|---|---|---|
| | 1 | 2 | 3 | 4 | 5 | 6 |
| 0.00 | 2 | 4 | 6 | 8 | 10 | 10 |
| 0.25 | 1 | 2 | 4 | 4 | 6 | 8 |
| 0.50 | 0 | 0 | 1 | 1 | 2 | 2 |
| 2.50 | 0 | 0 | 0 | 0 | 0 | 0 |
| 5.00 | 0 | 0 | 0 | 0 | 0 | 0 |

Mode of Action

Although it is understood that the following is not to be construed as a limitation, the mode of operation of the invention can be explained in terms of the slow release of the active biocidal copolymer from a natural reservoir formed by the masonry or wood construction material that has been treated. Thus, when the aqueous biocidal copolymer composition is applied to an exterior masonry surface, the treatment composition is absorbed into the pore space of the masonry and the masonry matrix functions as a reservoir for the long-term release of copolymer.

During dry seasons, the masonry pore equilibrium moisture content decreases; the copolymer concentrates and adsorbs to the pore surface. The mobility of the biocidal copolymer to the exterior surface is reduced. However, at the same time, surface algal growth is inhibited by the reduction in available water and there is a concurrent reduction in the requirement for biocide at the exterior masonry surface.

As a wet season approaches, the humidity increases; the moisture content of the masonry increases; the percent of pore volume saturated with water increases and the mass transport of biocidal copolymer to the exterior surface is enhanced. The end result of this transport is an increase in the quantity of biocide at the surface of the masonry at the same time the moisture content conditions become optimal for algal growth. The porous masonry matrix controls the release of the copolymer, which in turn controls the release of the biocidal aldehyde. Thus, the release of biocide occurs when the demand for protection is greatest.

During periods of heavy rain, copolymer at a non-coated exterior masonry surface can be removed by leaching. However, it has been shown that the diffusional transport to a masonry exterior surface is greatly reduced when it occurs via water-filled long narrow pores in a porous substance. As has been shown by the literature in the art, the flux of copolymer to the masonry surface is controlled by the pore size distribution, interconnectedness and tortuosity. In other words, even though a stream of water is flowing down an exterior masonry wall during heavy rain, the flux of biocide out of the wall may be minimal. Painting a copolymer treated masonry surface further attenuates the leaching effect of heavy rainfall.

I claim:

1. A method of providing a time-released algaecide to a porous surface of a masonry construction material selected from the group consisting of stone, concrete and brick, the method comprising:

a. contacting the porous surface of said masonry construction material with an aqueous biocidal composition of 2-propenal copolymer, said copolymer having a concentration of at least 0.5%, by weight;

b. maintaining said porous surface in contact with said algaecidal composition for a period of time sufficient to saturate a portion of the construction material with algaecidal composition, to a depth of about 1 to 5 cm, and c. allowing the surface of the construction material to dry, whereby the growth of algae on said masonry construction is inhibited.

2. The method of claim 1, wherein step (a) includes applying a biocidal composition from about 0.25% to about 5% by weight of the 2-propenal copolymer.

3. The method of claim 2, wherein the construction material forms a portion of a completed structure.

4. The method of claim 1, wherein the porous surface of the construction material to be treated is immersed in the aqueous biocidal composition for a predetermined period of time.

5. The method of claim 1, wherein the porous surface of the construction material to be treated is sprayed with the aqueous biocidal composition.

6. The method of claim 5, wherein the spraying is repeated.

7. The method of claim 1, wherein the porous biocidal composition is applied in the form of a continuous stream.

8. The method of claim 1 which further comprises applying at least one architectural coating to the porous surface of the construction material after step (c).

9. The method of claim 1, wherein the concentration of the 2-propenal copolymer in the construction material is about 0.01 to 1.0 gm of 2-propenal copolymer per gram of construction material after the drying of step (c).

10. The method of claim 1 wherein the construction material is contacted with the biocidal composition in a treatment zone.

11. The method of claim 10, wherein the treatment zone comprises a dip tank.

12. The method of claim 10, wherein the treatment zone comprises a liquid sprayer.

13. The method of claim 10, wherein the treatment zone comprises a pressurized chamber.

14. A porous masonry construction material selected from stone, concrete or brick that is resistant to surface defacement by algal growth containing an aqueous, algicidal composition of 2-propenal copolymer having a concentration of at least 0.5%, by weight, in a portion of the porous material extending from the surface exposed to algal defacement to a depth of about 1 to 5 cm.

15. The construction material of claim 14 in which the surface subject to algal defacement is covered by an architectural coating.

16. The construction material of claim 14, wherein the 2-propenal copolymer extends below all of the exterior porous surfaces of the construction material.

17. The construction material of claim 14, wherein the construction material has major and minor surfaces and the biocidal composition contacts at least one of the major surfaces.

* * * * *